United States Patent [19]

Nakanishi et al.

[11] 4,440,856

[45] Apr. 3, 1984

[54] PROCESS FOR PRODUCING L-GLUTAMIC ACID

[75] Inventors: Toshihide Nakanishi, Hofu; Mamoru Kohata, Kawasaki; Minoru Sakurai, Hofu, all of Japan

[73] Assignee: Kyowa Hakko Kogyo Co., Ltd., Tokyo, Japan

[21] Appl. No.: 331,312

[22] Filed: Dec. 16, 1981

[51] Int. Cl.³ .................. C12P 13/18; C12R 1/13; C12R 1/15; C12N 1/20
[52] U.S. Cl. ................... 435/111; 435/253; 435/840; 435/843
[58] Field of Search ............... 435/110, 111, 112, 253

[56] References Cited

U.S. PATENT DOCUMENTS 3,123,537  3/1964  Miescher .................. 435/110
3,326,775  6/1967  Miescher .................. 435/112

FOREIGN PATENT DOCUMENTS 52-66687  6/1977  Japan ..................... 435/110
53-8798   3/1978  Japan ..................... 435/111

OTHER PUBLICATIONS

Momose et al., Agricultural and Biological Chemistry, vol. 42, No. 10, pp. 1911-1917, (1978).

Primary Examiner—Lionel M. Shapiro
Attorney, Agent, or Firm—Fitzpatrick, Cella, Harper & Scinto

[57] ABSTRACT

L-glutamic acid is produced by culturing a mutant microorganism belonging to the genus Corynebacterium or Brevibacterium which mutant is temperature-sensitive remediable with an unsaturated higher fatty acid. L-glutamic acid is recovered from the culture liquor.

11 Claims, No Drawings

PROCESS FOR PRODUCING L-GLUTAMIC ACID

BACKGROUND OF THE INVENTION

The present invention relates to a process for producing L-glutamic acid by fermentation and more specifically, to a process for producing L-glutamic acid, by culturing an L-glutamic acid producing microorganism belonging to the genus Corynebacterium or Brevibacterium which organism has been mutated to acquire a temperature-sensitivity remediable with an unsaturated higher fatty acid.

A heretofore known microorganism capable of producing L-glutamic acid generally requires biotin to show adequate growth, while for the purpose of accumulating L-glutamic acid in a medium, the amount of biotin to be contained in a medium must be limited, or a substance which inhibits the action of biotin, such as is described in Japanese Published Examined Patent Application Nos. 1695/'65 and 8798/'65, must be added where a biotin-rich medium is used.

Those methods utilizing of such microorganism suffer from a number disadvantages. For example, in case of the method of limiting the amount of biotin in the fermentation medium the utilization of carbon sources, particularly inexpensive molasses is inevitably restricted; and that in case of the method of adding a substance which inhibits the action of biotin, the point addition and the amount of the substance constitute important factors and it is difficult to control the cultivation process.

The following operations wherein the production of L-glutamic acid is independent of the amount of biotin in the nutrient medium are also known.

One such process for producing L-glutamic acid by fermentation employs a microorganism belonging to the genus Corynebacterium which needs, for its growth or multiplication, not biotin but rather an unsaturated higher fatty acid such as oleic acid (Japanese Published Examined Patent Application No. 19632/75). The application also refers to a strain belonging to the genus Brevibacterium having similar properties to the Corynebacterium strain. This process, however, suffers from the economic and procedural disadvantage in that it is necessary to add to the medium an unsaturated higher fatty acid such as oleic acid whose cost is relatively high and to control the point of addition and the amount of the said compound. Alternatively, a process is known for producing L-glutamic acid by fermentation of a mutant belonging to the genus Brevibacterium whose growth is more likely to be influenced by temperature than the parent strain, as disclosed in Japanese Published Unexamined Patent Application No. 66687/77. It is reported that said microorganism has no requirement for oleic acid in Agricultural Biological Chemistry, 42 (10), 1911 (1978). Further, the yield is poor in terms of the productivity of L-glutamic acid to glucose. Thus, a need exists for a more reliable and economic method for the production of L-glutamic acid by fermentation techniques.

SUMMARY OF THE INVENTION

It has now been found that by leading an L-glutamic acid producing microbial strain to mutagenesis, a mutant organism may be obtained with temperature-sensitivity remediable with an unsaturated higher fatty acid, and which produces, upon fermentation, L-glutamic acid in excellent yields in a biotin-rich medium. In other words, the finding by the present inventors of a mutant whose requirement for an unsaturated higher fatty acid manifests itself above a certain temperature, enables the production of L-glutamic acid in a good yield without the necessity of adding a substance for inhibition of the action of biotin and unsaturated higher fatty acids such as oleic acid to a biotin-rich medium.

Thus, in accordance with the present invention, L-glutamic acid is produced by culturing a temperature-sensitive remediable with an unsaturated fatty acid mutant L-glutamic acid producing microorgnism belonging to the genus Corynebacterium or Brevibacterium, in a nutrient medium containing biotin until L-glutamic acid is accumulated in the culture liquor and thereafter recovering said L-glutamic acid therefrom.

DESCRIPTION OF THE INVENTION

In accordance with the present invention, any L-glutamic acid producing microorganism with temperature-sensitivity remediable with an unsaturated higher fatty acid and belonging to the genus Corynebacterium or Brevibacterium may be used. Said temperature-sensitive strain is a mutant which needs an unsaturated higher fatty acid to show growth or as adequate growth as the parent strain in a high temperature environment wherein the parent strain can grow and which needs no unsaturated higher fatty acid to show as adequate growth as the parent strain in a low temperature environment. A microorganism is preferred which shows as adequate growth as the parent strain at a temperature lower than 34° C. and which needs an unsaturated higher fatty acid to show growth or as adequate growth as the parent strain at 34° C. or more.

As the unsaturated higher fatty acid, those having 16-22 carbon atoms such as oleic acid, linolic acid, linolenic acid, ricinoleic acid, arachidonic acid, palmitoleinic acid, erucic acid, and the like are appropriate.

The mutant microorganism useful in carrying out the present invention can be obtained either by artificial means such as ultraviolet irradiation, X-ray irradiation and treatment with various chemical mutagens such as nitrosoguanidine and ethylmethanesulfonate or by spontaneous mutation. After the mutation inducing treatment, a mutant is selected which requires an unsaturated higher fatty acid to show growth or as adequate growth as the parent strain in a high temperature environment wherein the parent strain can grow, e.g. at 38° C., and simultaneously, requires no unsaturated higher fatty acid to show as adequate growth as the parent strain in a low temperature environment such as at 28°–34° C.

Examples of thus obtained temperature-sensitive mutants remediable with an unsaturated higher fatty acid are Corynebacterium glutamicum H 2874 (FERM-P No. 5741, NRRL B-12304) induced from Corynebacterium glutamicum ATCC 13032 and Brevibacterium lactofermentum H 2875 (FERM-P No. 5742, NRRL B-12305) induced from Brevibacterium lactofermentum ATCC 13869. Such mutant strains have been deposited with the United States Department of Agriculture, Peoria, Ill. under the above-noted accession numbers and are available to the public. While these strains are presently preferred, it will be understood that any L-glutamic acid producing mutant having the desired temperature-sensitivity remediably with an unsaturated higher fatty acid and which is derived from an L-glutamic acid producing parent strain belonging to the genus Corynebacterium or Brevibacterium is contemplated by the present invention.

As an example of a method for obtaining a suitable mutant, *Corynebacterium glutamicum* ATCC 13032 or *Brevibacterium lactofermentum* ATCC 13869 is cultured in a bouillon medium at 28° C. for 12 hours and the culture liquor is subjected to centrifugation. The collected cells are washed twice with TM-buffer (pH 6.0) comprising 6 g/l tris.aminomethane, 5.8 g/l maleic acid, 1 g g/l ammonium sulfate, 5 mg/l CaCl$_2$.2H$_2$O, 0.1 g/l MgSO$_4$.7H$_2$O and 0.25 mg/l FeSO$_4$.7H$_2$O and then suspended in the same buffer at a density of about $10^8$ cells/ml. To the suspension is added N-methyl-N'nitro-N-nitrosoguamidine to a final concentration of 0.5 mg/ml. The mixture is allowed to stand at 28° C. for 30 minutes and is then subjected to centrifugation. The collected cells are washed twice with TM-buffer and resuspended in the same buffer at a density of about $2 \times 10^8$ cells/ml. The suspension is added at a rate of 10% by volume to a minimal medium (pH 7.2) containing 1 g/l casamino acid. The minimal medium comprises 20 g/l glucose, 0.5 g/l potassium dihydrogen phosphate, 1 g/l dipotassium hydrogen phosphate, 4 g/l ammonium sulfate, 2 g/l urea, 30 μg/l biotin, 100 μg/l thiamine HCl, 0.5 mg/l nicotinic acid amide, 0.5 mg/l calcium pantothenate, 0.1 g/l magnesium sulfate.7H$_2$O, 10 mg/l ferrous sulfate.7H$_2$O, 4 mg/l manganese sulfate.4H$_2$O and 50 mg/l calcium chloride.2H$_2$O. Culturing with shaking at 28° C. is carried out for 2 hours. To the resulting culture liquor is added an equal amount of minimal medium containing 400 g/l sucrose and 0.02 M MgSO$_4$ and culturing is then continued with shaking at 37° C. for an additional one hour.

Then, penicillin G is added to a final concentration of 500 μ/ml, and after 90 minutes of incubation, the resulting solution is cooled and subjected to centrifugation. The collected cells are washed with TM-buffer and suspended in the same buffer at a density of about $10^5$ cells/ml. The suspension is spread onto bouillon-agar plates and large colonies formed by incubating these plates at 37° C. for 2 days are marked. Incubation is then continued at 28° C. for 2 days to isolate newly formed colonies.

The colonies are replicated on two minimal agar plates and one minimal agar plate containing 50 mg/l sodium oleate. One of the two minimal agar plates is incubated at 28° C. and the other two at 37° C. for 48 hours. Strains which are able to grow both on a sodium oleate-containing minimal agar plate at 37° C. and on a minimal agar plate at 28° C. but not on a minimal agar plate at 37° C. are isolated as mutants with temperature-sensitivity remediable with oleic acid. Two such strains are designated as H 2874 and H 2875.

The above treatments are all conducted under sterile conditions.

Table 1 shows the result of an experiment wherein the strains H 2874 and 2875, and the parent strains thereof are tested for the degree of temperature-sensitivity.

A medium comprising the following components is used for each cultivation:

| glucose | 20 g/l |
| potassium dihydrogen phosphate | 0.5 g/l |
| dipotassium hydrogen phosphate | 1 g/l |
| ammonium sulfate | 4 g/l |
| urea | 2 g/l |
| biotin | 30 μg/l |
| thiamine.HCl | 100 μg/l |
| nicotinic acid amide | 0.5 mg/l |
| calcium pantothenate | 0.5 mg/l |
| magnesium sulfate.7H$_2$O | 0.1 g/l |
| ferrous sulfate.7H$_2$O | 10 mg/l |
| manganese sulfate.4H$_2$O | 4 mg/l |
| calcium chloride.2H$_2$O | 50 mg/l |
| pH 7.2 | |

Culturing is carried out for 12 hours in each temperature environment using a monod type tube. The designations "+++", "++", "+", "±" and "−" indicate vigorous growth, a standard growth, a growth to some extent, small growth and no growth, respectively.

TABLE 1

| Strain | Additive (100 mg/ml) | Growth 30° C. | 34° C. | 36° C. | 38° C. | 40° C. |
|---|---|---|---|---|---|---|
| H 2874 | — | +++ | ++ | ± | − | − |
| | Oleic acid | +++ | +++ | ++ | + | ± |
| | Linoleic acid | +++ | +++ | ++ | + | ± |
| ATCC 13032 | — | +++ | +++ | ++ | + | ± |
| | Oleic acid | +++ | +++ | ++ | + | ± |
| H 2875 | — | +++ | ++ | ± | − | − |
| | Oleic acid | +++ | +++ | ++ | + | ± |
| | Linoleic acid | +++ | +++ | ++ | + | ± |
| ATCC 13869 | — | +++ | +++ | ++ | + | ± |
| | Oleic acid | +++ | +++ | ++ | + | ± |

The microbiological properties of the species of *Corynebacterium glutamicum* and *Brevibacterium lactofermentum* are described in U.S. Pat. Nos. 3,003,925 and 3,117,915, respectively.

Either a synthetic or natural medium may be used for culturing of the microorganisms of the present invention so long as it contains a carbon source, a nitrogen source, inorganic materials and other nutrients which are assimilable by the strains utilized.

As a carbon source, carbohydrates such as sucrose, fructose, glucose, maltose, mannose, sorbitol, etc., sugar alcohols, starch, starch hydrolyzate, fruit juice, molasses, etc., various organic acids such as acetic acid, pyruvic acid, lactic acid, fumaric acid, etc., and lower alcohols such as ethanol, etc. may be used.

As a nitrogen source, ammonia, inorganic and organic ammonium salts such as ammonium chloride, ammonium sulfate, ammonium carbonate, ammonium phosphate, ammonium nitrate, ammonium acetate, etc., nitrogen-containing compound such as urea, etc., as well as nitrogenous organic materials such as peptone, meat extract, corn steep liquor, casein hydrolyzate, defatted soybean hydrolyzate, etc. may be used.

As inorganic materials, potassium phosphate, dipotassium hydrogenphosphate, magnesium sulfate, sodium chloride, ferrous sulfate, manganese sulfate, zinc sulfate and calcium carbonate, etc. are appropriate. Moreover, various vitamins such as biotin, nicotinic acid amide, thiamine, pantothenic acid, etc. which promote the growth of the strain may be added to the medium. However, where the compositions of the medium naturally includes these vitamins, it is unnecessary to supplement them individually. Particularly, since culturing of the mutant strains of the invention is to be in a biotin rich medium, such vitamin must be supplemented to the medium or supplied by another medium component such as cane molasses.

Culturing is generally carried out under aerobic conditions, e.g., with shaking or aeration-agitation at a temperature of 23°–42° C.

By using temperature-sensitive strains in accordance with the present invention the production of L-glutamic acid is dramatically effected using a biotin-rich medium. In other words, by culturing the present mutant strain in a low temperature environment wherein the strain shows adequate growth until multiplication proceeds to a certain extent and when the growth rate of the strain reaches a desired level, shifting the temperature to a higher temperature at which the growth of the strain is reduced without an unsaturated higher fatty acid, L-glutamic acid production can be realized in a biotin-rich medium without any chemical control such as the addition of reagents which inhibit the activity of biotin. The production of L-glutamic acid in a high yield in a biotin-rich medium requires so-called starved conditions whether the medium contains unsaturated higher fatty acids or not.

To investigate the low temperature suitable for the multiplication of the mutant to be used, the mutant is cultured at different temperatures using a biotin-rich medium, that is, a medium containing 20 μg/l biotin or more. Usually, a suitable temperature is 28°–34° C.

As the high temperature suitable for production of L-glutamic acid, a temperature at which the mutant cannot multiply without an unsaturated higher fatty acid and can produce L-glutamic acid in a high yield is selected, which is usually 34°–42° C.

The growth rate of the strain at which the temperature shift is made is equal to or a bit lower than the growth rate at which the parent strain shows the highest productivity of L-glutamic acid. It is generally difficult to inhibit the multiplication of the strain immediately after the temperature shift. The behavior of the productivity of L-glutamic acid after the temperature shift and the optimal temperature for the temperature shift have to be investigated in advance to know the desirable conditions for production of L-glutamic acid. The preferable point of temperature shift usually stands from the middle stage to the late stage in he logarithmic phase of the strain used.

During culturing, the pH is maintained at 6–9 and culturing is usually continued for 24–72 hours, or until significant amounts of L-glutamic acid is accumulated in the culture liquor.

At the completion of culturing, the recovery of L-glutamic acid from the culture liquor is carried out by conventional methods such as by ion exchange resin or direct crystallization.

Certain specific embodiments of the present invention are illustrated by the following representative examples which have actually been carried out.

EXAMPLE 1

In this example, cultures of the strains identified in the following Table 2 are inoculated into seed media (pH 7.2, before sterilization) comprising 50 g/l glucose, 10 g/l peptone, 5 g/l yeast extract, 5 g/l meat extract, 5 g/l ammonium sulfate, 1 g/l potassium dihydrogen phosphate, 1 g/l dipotassium hydrogen phosphate, 0.5 g/l magnesium sulfate.7H$_2$O, 20 mg/l ferrous sulfate.7H$_2$O, 20 mg/l manganese sulfate.4H$_2$O, 50 μg/l biotin and 5 g/l urea and cultured at 30° C. for 16 hours. Then, 4 ml of the seed culture liquor is put into a 250 ml-Erlenmeyer flask containing 20 ml of a culture medium (pH 6.5, before sterilization) comprising 60 g/l glucose, 5 g/l urea, 2 g/l ammonium sulfate, 1 g/l potassium dihydrogen phosphate, 1 g/l dipotassium hydrogen phosphate, 20 mg/l manganese sulfate 4H$_2$O, 100 μg/l biotin, 10 mg/l phenol red and sodium oleate having the concentrations identified in Table 2 and culturing is carried out at either 28° or 38° C. During culturing, 10% aqueous urea is added in 1 ml portions when the pH of the culture liquor is around 7.0 judging from the tone of the phenol red, and culturing is continued for 30 hours.

TABLE 2

| | Strain | H 2874 | | ATCC 13032 (parent strain) | H 2875 | | ATCC 13869 (parent strain) |
|---|---|---|---|---|---|---|---|
| | Additive (the amount) | No addition | Sodium oleate (200 mg/l) | No addition | No addition | Sodium oleate (200 mg/l) | No addition |
| 28 °C. | Cell concentration (OD) | 0.490 | 0.450 | 0.640 | 0.560 | 0.530 | 0.610 |
| | L-glutamic acid (g/l) | trace | 1.1 | trace | 2.6 | 4.3 | 2.1 |
| 38 °C. | Cell concentration (OD) | 0.230 | 0.380 | 0.415 | 0.275 | 0.310 | 0.380 |
| | L-glutamic acid (g/l) | 26.8 | 13.7 | 11.3 | 25.0 | 15.4 | 6.6 |

EXAMPLE 2

In this example, the same seed culture liquor as obtained in Example 1 is subject to a main fermentation in the same manner as described in Example 1 except that instead of glucose and biotin, the medium contains 60 g/l, converted to the corresponding amount of glucose, of cane molasses; and in that the concentration of sodium oleate and the culture temperatures are as identified in Table 3.

TABLE 3

| | Strain | H 2874 | | H 2875 | |
|---|---|---|---|---|---|
| | Additive (added amount) | No addition | Sodium oleate (400 mg/l) | No addition | Sodium oleate (400 mg/l) |
| 30 °C. | Cell concentration (OD) | 0.605 | 0.610 | 0.630 | 0.625 |
| | L-glutamic acid (g/l) | 0.1 | 2.5 | 1.4 | 2.7 |
| 38 °C. | Cell concentration (OD) | 0.345 | 0.460 | 0.320 | 0.410 |
| | L-glutamic acid (g/l) | 28.3 | 8.0 | 23.8 | 5.1 |

EXAMPLE 3

In this example, using the same seed medium and the same culture medium, excluding the addition of sodium oleate, as described in Example 1, one ml of the seed culture liquor is put into a 250 ml-Erlenmeyer flask containing 20 ml of a culture medium and culturing is carried out at 30° C. for 8 hours. Then, the temperature is shifted from 30° C. to those temperatures identified in Table 4 and culturing is continued for 35 hours. The amounts of L-glutamic acid accumulated in the culture liquor are as given in Table 4.

TABLE 4

| Shifted temperature | H 2874 L-glutamic acid (g/l) | H 2875 L-glutamic acid (g/l) |
| --- | --- | --- |
| 34° C. | 0.6 | 2.9 |
| 36 | 9.2 | 10.5 |
| 38 | 26.5 | 25.2 |
| 40 | 25.8 | 24.4 |
| 42 | 14.9 | 16.5 |

What is claimed is:

1. A process for producing L-glutamic acid which comprises:
   culturing an L-glutamic acid producing mutant microorganism belonging to the genus Corynebacterium or Brevibacterium in a biotin-rich nutrient medium until L-glutamic acid is accumulated in the culture liquor and thereafter recovering said L-glutamic acid therefrom;
   said mutant microorganism being temperature-sensitive remediable with an unsaturated higher fatty acid;
   said culturing step being carried out, at least in part, at a temperature at which said mutant requires the presence of said unsaturated higher fatty acid for growth or growth comparable to its parent strain at the said temperature;
   and
   said nutrient medium being essentially free of said unsaturated higher fatty acid.

2. A process according to claim 1, wherein said microorganism belongs to the species *Corynebacterium glutamicum* or *Brevibacterium lactofermentum*.

3. A process according to claim 2 wherein said microorganism has the identifying characteristics of *Corynebacterium glutamicum* NRRL B-12304.

4. A process according to claim 2 wherein said microorganium has the identifying characteristics of *Brevibacterism lactofermentum* NRRL B-12305.

5. A process according to claim 1 wherein said microorganism is *Corynebacterium glutamicum* NRRL B-12304.

6. A process according to claim 1 wherein said microorganism is *Brevibacterium lactofermentum* NRRL B-12305.

7. A process according to claim 1 wherein said unsaturated higher fatty acid is selected from the group consisting of oleic acid, linolic acid, linolenic acid, ricinoleic acid, arachidonic acid, palmit-oleinic acid and erucic acid.

8. A process according to claim 1 wherein said culturing step is carried out at a temperature of from 23° to 42° C.

9. A process according to claim 8 wherein said culturing step is initially carried out at a temperature of from 28° to 34° C. and then shifted to a temperature of from 34° to 42° C.

10. A biologically pure culture of the microorganism *Corynebacterium glutamicum* NRRL B-12304, which microorganism when cultured produces L-glutamic acid.

11. A biologically pure culture of the microorganism *Brevibacterium lactofermentum* NRRL B-12305 which microorganism when cultured produces L-glutamic acid.

* * * * *

UNITED STATES PATENT AND TRADEMARK OFFICE
CERTIFICATE OF CORRECTION

PATENT NO. : 4,440,856

DATED : April 3, 1984

INVENTOR(S) : TOSHIHIDE NAKANISHI, et al.

It is certified that error appears in the above-identified patent and that said Letters Patent is hereby corrected as shown below:

Cover page, left column, add:

--Foreign Application Priority Data:
December 17, 1980  Japan  177123/80--

Column 1, line 22, delete "of" before "such"

Column 1, line 23, insert --of-- following "number"
Column 2, line 12, change "microorgnism" to --microorganism--
Column 3, line 11, delete "g" before "g/l"
Column 5, line 42, change "he" to --the--

Signed and Sealed this

Sixth Day of November 1984

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,440,856
DATED      : April 3, 1984
INVENTOR(S) : TOSHIHIDE NAKANISHI, ET AL.

It is certified that error appears in the above-identified patent and that said Letters Patent is hereby corrected as shown below:

Column 8, line 5, change "microorganium" to:
--microorganism--

Column 8, line 6, change "Brevibacterism" to:
--Brevibacterium--.

Signed and Sealed this

Fifteenth Day of January 1985

[SEAL]

*Attest:*

*Attesting Officer*

GERALD J. MOSSINGHOFF
*Commissioner of Patents and Trademarks*